United States Patent [19]

Mattson et al.

[11] Patent Number: 5,530,012
[45] Date of Patent: Jun. 25, 1996

[54] 3-ALKOXYBENZYLPIPERIDINE DERIVATIVES AS MELATONERGIC AGENTS

[75] Inventors: Ronald J. Mattson, Meriden; John D. Catt, Southington; Daniel J. Keavy, Middletown, all of Conn.

[73] Assignee: Bristol-Myers Squibb Co., Princeton, N.J.

[21] Appl. No.: 362,337

[22] Filed: Dec. 22, 1994

[51] Int. Cl.$^6$ ................ A61K 31/445; C07D 211/06
[52] U.S. Cl. ............................................ 514/330; 546/226
[58] Field of Search ............................... 546/226; 514/330

[56] References Cited

U.S. PATENT DOCUMENTS

| | | | |
|---|---|---|---|
| 4,719,219 | 1/1988 | Arvidsson et al. | 514/317 |
| 5,071,875 | 12/1991 | Horn et al. | 514/613 |
| 5,194,614 | 3/1993 | Andrieux et al. | 544/400 |
| 5,225,442 | 7/1993 | Andrieux et al. | 514/613 |
| 5,240,919 | 8/1993 | Yous et al. | 514/210 |
| 5,300,507 | 4/1994 | Yous et al. | 514/253 |
| 5,308,866 | 5/1994 | Lesieur et al. | 514/469 |
| 5,318,994 | 6/1994 | Andrieux et al. | 514/613 |
| 5,322,843 | 6/1994 | Yous et al. | 514/233.8 |
| 5,322,849 | 6/1994 | Yous et al. | 514/321 |
| 5,326,775 | 7/1994 | Yous et al. | 514/375 |

FOREIGN PATENT DOCUMENTS

| | | |
|---|---|---|
| 646968 | 8/1992 | Australia . |
| 48729/93 | 4/1994 | Australia . |
| 0532177A1 | 8/1992 | European Pat. Off. . |
| WO9407487 | 4/1994 | WIPO . |

OTHER PUBLICATIONS

*Lange's Handbook of Chemistry*, Section 1, Table 1.16 (1972).

Cardellini et al. "Interaction of some 2–hydroxybenzylpiperidines with dopamine receptors" Farmaco Ed. Sc. v. 42, pp. 307–317 (1987).

Cassone et al, "Dose–Dependent Entrainment of Rat Circadian Rhythms by Daily Injection of Melatonin", *J. Biol. Rhythms*, vol. 1., No. 3, (1986) pp. 219–229.

Arendt et al, "Alleviation of Jet Lag by Melatonin: preliminary results of controlled double blind trial", *Br. Med. J.* vol. 292, 1986) p. 1170.

Begue et al, "Synthèses dans la sèrie de l'aza–2 bicyclo[2,2,2]octane (isoquinuclidine)", *Bulletin de La Societe Chimque de France*, No. 3, (1969) pp. 781–787. (French).

*Primary Examiner*—Ceila Chang
*Attorney, Agent, or Firm*—Sandra M. Nolan

[57] ABSTRACT

Novel 3-alkoxybenzylpiperidines have melatonergic properties. They are believed useful in treating depression, jet-lag, work-shift syndrome, sleep disorders, glaucoma, some disorders associated with reproduction, cancer, immune disorders and neuroendocrine disorders.

20 Claims, No Drawings

3-ALKOXYBENZYLPIPERIDINE DERIVATIVES AS MELATONERGIC AGENTS

BACKGROUND OF THE INVENTION

The invention pertains to novel 3-alkoxybenzylpiperidine derivatives (i.e., amides and ureas of 3- and 4-benzylpiperidines) having drug and bio-affecting properties and to their preparation, pharmaceutical formulations containing them, and methods of use. In particular, the invention concerns N-acyl 3-benzylpiperidines and N-amido 4-benzylpiperidines having a meta-alkoxy substituent in the phenyl ring of the benzyl moiety. These compounds possess melatonergic properties that should make them useful in treating certain medical disorders.

Melatonin (i; N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms, and the modulation of retinal physiology.

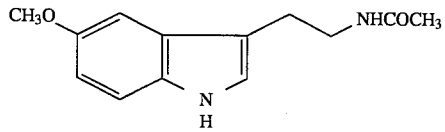
i

Recent evidence demonstrates that melatonin exerts its biological effects through specific receptors. Use of the biologically active, radiolabelled agonist [$^{125}$I]-2-iodomelatonin has led to the identification of high affinity melatonin receptors in the central nervous systems (CNS) of a variety of species. The sequence of one such high affinity melatonin receptor, cloned from frog melanocytes, has been reported. In mammalian brain, autoradiographic studies have localized the distribution of melatonin receptors to a few specific structures.

Although there are significant differences in melatonin receptor distribution between closely related species, in general the highest binding site density occurs in discrete nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487. Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, work-shift syndrome, sleep disorders, glaucoma, reproduction, cancer, immune disorders, neuroendocrine disorders, and a variety of sleep disorders.

Aside from simple indole derivatives of melatonin itself, various amide structures have been prepared and their use as melatonin ligands disclosed. In general these amide structures can be represented as:

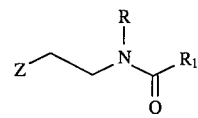
ii wherein Z is an aryl or heteroaryl system attached by a two carbon chain to the amide group. Some specific examples follow.

Yous, et al. in European Patent Application EPA 527 687A disclose as melatonin ligands arylethylamines 1,

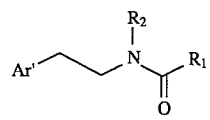
1 wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Horn and Dubocovich in European Patent Application EPA 420 064A disclose 2-amidotetralins 2 as melatonin ligands,

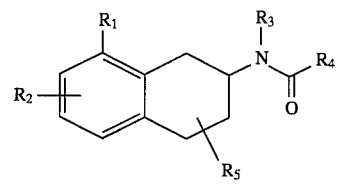
2 wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Yous, et al. in European Patent Application 506 539A claim melatonin ligands 3,

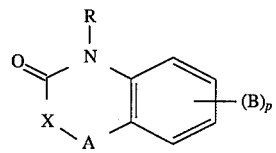
3 wherein A is oxygen or sulfur; X is a methylene group or a bond; and R is H or lower alkyl when p is 1 and B is defined by the radical 4,

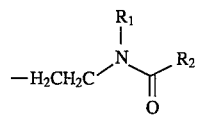
4 wherein $R_1$ is hydrogen or lower alkyl and $R_2$ is, inter alia, hydrogen, lower alkyl or cycloalkyl. Alternatively, R is defined by the radical 4 when p is 0 or 1 and B is lower alkoxy.

Several naphthalene derivatives have also been disclosed as melatonin ligands. Andrieux, et al. in European Patent Application 447 285A claim amidoalkylnaphthalenes 5.

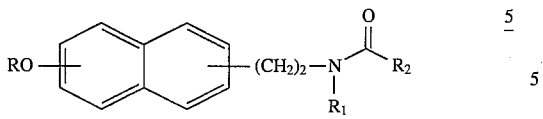

wherein R is lower alkyl; $R_1$ is hydrogen or lower alkyl; and $R_2$ is, inter alia, hydrogen, lower alkyl, or cycloalkyl.

Yous, et al. in European Patent Application 562 956A disclose amide and urea naphthalene derivatives 6,

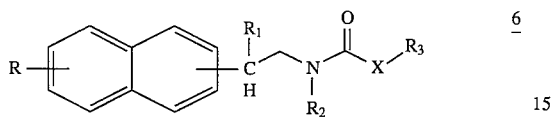

in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Lesieur, et al. in European Patent Application 530 087A disclose naphthylethylureas and naphthylethylthioureas 7,

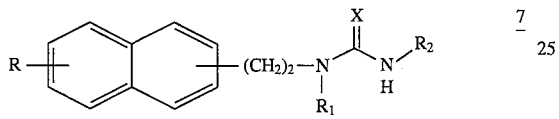

in which R is hydrogen or $OR_3$ wherein $R_3$ is, inter alia. hydrogen, lower alkyl, or cycloalkyl; $R_1$ is hydrogen or lower alkyl; X is oxygen or sulfur; and $R_2$ is, inter alia, lower alkyl or cycloalkyl.

Finally, Langlois, et al., in Australian Patent Application AU-A-48729/93 disclose arylalkyl(thio)amides 8 as melatonergic ligands,

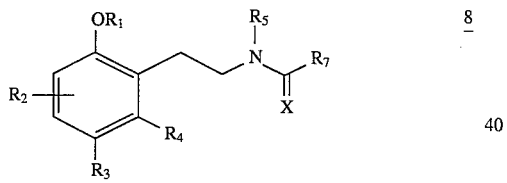

wherein $R_1$ is hydrogen or lower alkyl; $R_2$ is hydrogen, halogen, or lower alkyl; $R_3$ and $R_4$ are identical or different groups including, inter hydrogen, halogen, or lower alkyl; $R_5$ is hydrogen or lower alkyl; X is sulfur or oxygen and $R_7$ is, inter alia, lower alkyl or alkenyl.

However these references do not teach or suggest the novel melatonergic alkoxybenzylpiperidine derivatives of the present invention. There are few reported examples of compounds bearing an alkoxy-substituted benzyl moiety appended to the 3- or 4-position of an N-acyl piperidine. Begue and Fetizon describe the synthesis of bridged piperidine derivatives 9 in *Bull. Soc. Chim. Fr.*, 1969, pp. 781–787.

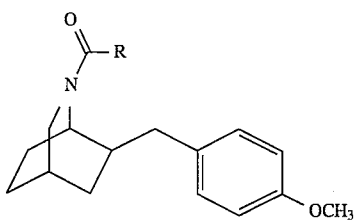

Jacobs et al. in European Patent Application 532177A disclose compounds of type 10 as intermediates in the synthesis of 11. Neither 9 nor 10 were described as having melatonergic properties.

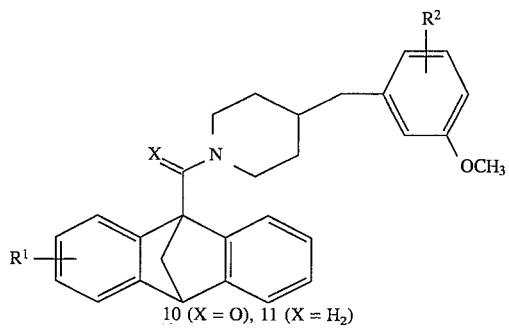

SUMMARY AND DETAILED DESCRIPTION OF THE INVENTION

In its broadest aspect, the present invention is concerned with compounds of Formula I, which possess melatonergic properties and thus have potential utility in the treatment of conditions affected by melatonin activity.

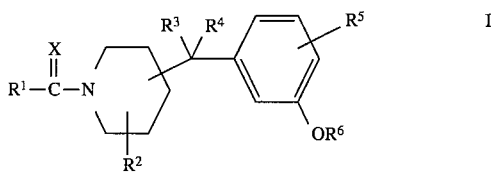

In Formula I: $R^1$ is $C_{1-4}$ alkyl, $C_{2-4}$ alkenyl, $C_{3-6}$ cycloalkyl or $NR^7R^8$ where $R^7$ and $R^8$ are independently selected from hydrogen and $C_{1-4}$ alkyl, but $R^7$ and $R^8$ cannot both be hydrogen; $R^2$, $R^3$ and $R^4$ are independently hydrogen or $C_{1-4}$ alkyl; $R^5$ is hydrogen, $C_{1-4}$ alkyl, halogen or trifluoromethyl; $R^6$ is $C_{1-4}$ alkyl; X is either oxygen or sulfur; the benzyl group is appended to either the 3- or 4-position of the piperidine ring.

It is to be understood that, as used herein, halogen denotes fluorine, chlorine, bromine and iodine; the term "$C_{1-4}$ alkyl" refers to straight and branched chain saturated carbon radicals of from 1 to 4 carbon atoms, e.g. methyl, ethyl, n-propyl, 1-methyl-1-ethyl, 1-methyl-l-propyl,; "alkenyl" refers to straight and branched carbon radicals of from 2 to 4 carbon atoms containing a carbon-carbon double bond, e.g. ethenyl, propenyl; "cycloalkyl" pertains to homocyclic rings of from 3 to 6 carbon atoms, e.g. cyclopropyl, cyclobutyl, cyclopentyl. By "$NR^7R^8$" is meant alkylamino groups wherein $R^7$ is and $R^8$ are independently selected from H and $C_{1-4}$ alkyl, with the proviso that $R^7$ and $R^8$ are not both hydrogen.

In a narrower aspect, the present invention pertains to compounds of Formula I in which $R^2$, $R^3$ and $R^4$ are hydrogen; $R^5$ is either hydrogen or 2-fluoro, with the proviso that when $R^5$ is 2-fluoro the alkoxy group is para to the fluoro group; and $R^6$ is methyl.

Based upon biological tests, the following Formula I compounds are preferred. All have $ML_1$ activity of 250 nM or less.

Preferred compounds of Formula I are those wherein X is O; $R^2$, $R^3$ and $R^4$ are all H; $R^5$ is H or 2-fluoro, and $R^6$ is $CH_3$.

More preferred compounds of the present invention include those in the following list:

1-(Cyclopropylcarbonyl)-4-[(2-fluoro-5-methoxyphenyl)methyl]piperidine;

4-[(2-Fluoro-5-methoxyphenyl)methyl]-1-(1-oxobutyl)piperidine;
4-[(2-Fluoro-5-methoxyphenyl)methyl]-1-(1-oxopropyl)piperidine;
4-[(2-Fluoro-5-methoxyphenyl)methyl]-1-(1-oxo-2-propenyl)piperidine;
1-(Cyclobutylcarbonyl)-4-[(2-fluoro-5-methoxyphenyl)methyl]piperidine;
4-[(2-Fluoro-5-methoxyphenyl)methyl]-N,N-dimethyl-1-piperidinecarboxamide;
1-(Cyclopropylcarbonyl)-4-[(3-methoxyphenyl)-methyl]piperidine;

4-[(2-Fluoro-5-methoxyphenyl)methyl]-N-propyl-1-piperidinecarbothioic acid amide;
3-[(3-Methoxyphenyl)methyl]-1-(1-oxobutyl)piperidine; and
N-Ethyl-3-[(3-methoxyphenyl)methyl]-1-piperidine-carboxamide.

The compounds of Formula I can be prepared as depicted in the following General Scheme. The groups $R^1$, $R^2$, $R^3$ and X shown in Scheme 1 are as defined hereinabove. The additional symbol M appearing in Scheme 1 represents a metal such as magnesium or lithium of a Grignard or organolithium reagent respectively.

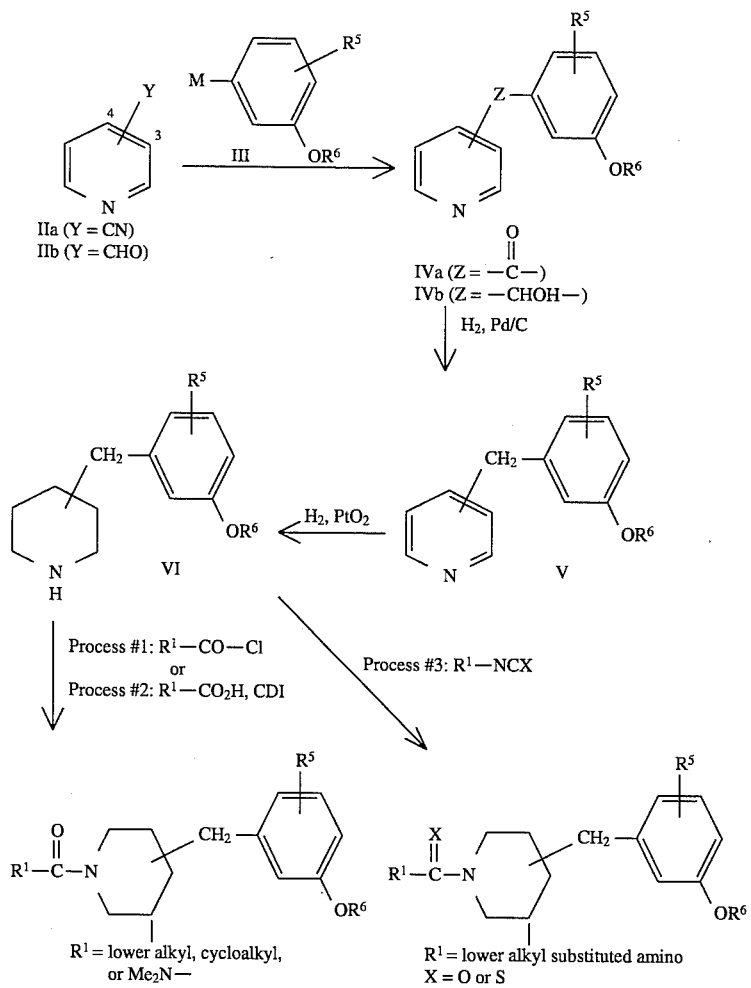

General Scheme

4-[3-Methoxyphenyl)methyl]-1-(1-oxobutyl)piperidine
4-[(2-Fluoro-5-methoxyphenyl)methyl]-1-(2-methyl-1-oxobutyl)piperidine;
N-Ethyl-4-[(3-methoxyphenyl)methyl]-1-piperidinecarboxamide;
4-[(3-Methoxyphenyl)methyl]-N-methyl-1-piperidinecarboxamide;
4-[(2-Fluoro-5-methoxyphenyl)methyl]-N-methyl-1-piperidinecarboxamide;
4-[(2-Fluoro-5-methoxyphenyl)methyl]-N-propyl-1-piperidinecarboxamide;
N-Ethyl-4-[(2-fluoro-5-methoxyphenyl)methyl]-1-piperidinecarboxamide;

The preparation of Compounds of Formula I comprises the following steps:

(1) Treatment of the commercially available 3-or 4-cyanopyridine, IIa, with an organometallic reagent, III, followed by hydrolysis to afford the ketone intermediate of Formula IVa. Alternatively, 3- or 4-pyridine carboxaldehyde, IIb, can be treated with the reagent, III, to give the alcohol intermediate, IVb.

(2) Catalytic reduction of either intermediates IVa or IVb in the presence of palladium on carbon catalyst to provide the benzylpyridine intermediates of Formula V.

(3) Hydrogenation of the pyridine ring of the benzylpyridines V in the presence of platinum oxide catalyst under acidic conditions to afford the intermediates of Formula VI.

(4) Compounds of Formula I wherein $R^1$ is lower alkyl or cycloalkyl and X is oxygen can be prepared by either Process #1 which entails N-acylation of intermediates of Formula VI with an acyl chloride or carbamoyl chloride; or via Process #2 in which the intermediates of Formula VI undergo reaction with the appropriate carboxylic acid in the presence of carbonyl diimidazole (CDI) as a condensing agent. Process #3 entails the reaction of intermediates VI with either an alkyl isocyanate or isothiocyanate to afford urea or thiourea derivatives of Formula I wherein $R^1$ is lower alkyl substituted amino and X is oxygen or sulfur respectively.

Reagents, solvents and reaction conditions for the above described preparative steps would be known to one skilled in the art of organic synthesis as all the steps are standard organic reactions having extensive precedent in the chemical literature.

These preparative methods may be varied in order to produce other compounds embraced by this invention but not specifically disclosed.

Additionally compounds of Formula I also encompass all pharmaceutically acceptable solvates, hydrates being the preferred solvates. The present invention also includes stereoisomers as well as optical isomers, e.g. mixtures of enantiomers as well as individual enantiomers and diastereomers, which arise as a consequence of structural asymmetry in certain compounds of the instant series. Separation of the individual isomers is accomplished by application of various methods which are well known to practitioners of the art.

The "Description of Specific Embodiments" section hereinbelow provides greater descriptive details of the synthesis of compounds of Formula I and of intermediates of Formulas IV–VI.

The compounds of the present invention have affinity for receptors of the endogenous pineal hormone, melatonin, as determined in a receptor binding assay, and exhibit partial agonist activity as determined by a functional assay; the biological tests are described hereinbelow. As has been discussed above, melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, immune disorders and neuroendocrine disorders.

The systemic administration and dosing regimen of compounds of Formula I can be considered to be done in a manner similar to that described for melatonin itself. The dosage and dosage regimen must be adjusted using sound professional judgment and taking into consideration such variables as the age, body weight, sex and physical condition of the recipient, the route of administration and the nature of the illness being treated. Oral, transdermal, subcutaneous, intravenous, intramuscular, rectal, buccal, intranasal, and ocular routes of administrations may be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatability, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, mineral oil and the like. Mixures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.90 to 90%, or other suitable amounts, of excipient(s).

Dosage levels will be dictated by the patient's needs and by the medical judgment of the treating physician. Generally, however, dosages of about 0.1 mg to about 100 mg per day are useful to treat sleep or circadian rhythm disorders.

In methods of treatment employing the compounds of the invention, the treatment will involve the step(s) of administering one or more dosages of the compound to a host, preferably a mammalian, e.g. human host in need of such treatment.

DESCRIPTION OF SPECIFIC EMBODIMENTS

The compounds which constitute the present invention, their methods of preparation and their biological actions will appear more fully after consideration of the following examples, which are given for the purpose of illustration only and are not to be construed as limiting the invention's scope.

In the following examples, temperatures are expressed in degrees Celsius (°C.), hours are designated "h" or "hr", and melting points are uncorrected. The proton and carbon nuclear magnetic resonance (NMR) spectral characteristics refer to chemical shifts ($\delta$) expressed as parts per million (ppm) versus tetramethylsilane (TMS) as the reference standard. The relative area reported for NMR signals at various chemical shifts corresponds to the number of hydrogen atoms of a particular type in the molecule. The multiplicities of the signals are reported as broad singlet (bs), singlet (s), is doublet (d), triplet (t), quartet (q) or multiplet (m). The NMR spectra were obtained using solutions of the compounds in either deuterodimethylsulfoxide (DMSO-$d_6$) or deuterochloroform (CDCl$_3$).

Infrared (IR) spectral descriptions include only absorption wave numbers (cm$^{-1}$) having functional group identification value and IR determinations were made using potassium bromide (KBr) as diluent. The elemental analyses are reported as percent by weight. Table 1 lists the IR carbonyl stretching frequencies and elemental analyses of all the specifically claimed compounds of Formula I.

The following examples describe in detail the preparation of representative examples of compounds of Formula I and of synthetic intermediates. It will be apparent to those skilled in the art that modifications, both of material and methods, will allow preparation of other compounds disclosed herein. From the foregoing description and the following examples it is believed that one skilled in the art is able to carry out the invention to the fullest extent.

A. PREPARATION OF INTERMEDIATES (IV)

EXAMPLE 1

4-[(3-Methoxyphenyl)methyl]piperidine
Step 1

A solution of 4-cyanopyridine (20.8 g, 200 mmol) in tetrahydrofuran (THF) was added to the Grignard reagent prepared from 3-bromoanisole (37.4 g, 200 mmol) and magnesium (4.8 g, 200 mmol) in THF (400 ml) at −78° C. The solution was allowed to warm to 25° C. and quenched with ammonium chloride solution. The organic layer was separated and washed with water and 3N hydrochloric acid. The acid washes were stirred for 0.5 hr and neutralized with 50% sodium hydroxide. The basic mixture was extracted with ether. The extracts were dried and concentrated in vacuo. The crude material was crystallized from hexane to give 4-(3-methoxybenzoyl)pyridine (27 g, 63%).

Step 2

Ammonium formate (25 g) was added to a mixture of 4-(3-methoxybenzoyl)pyridine (27 g, 127 mmol) and 10% palladium on charcoal (7 g) in acetic acid (250 ml). The mixture was heated at reflux for 0.5 hr. The mixture was cooled and diluted with an equal volume of methylene chloride. The catalyst was removed and the solution concentrated in vacuo. The residue was dissolved in water and basified with sodium hydroxide. The mixture was extracted with ether. The extracts were dried and concentrated in vacuo to give the crude 4-(3-methoxybenzyl)pyridine (25 g, 99%) which was used without purification in the next step.

Step 3

A mixture of 4-(3-methoxybenzyl)pyridine (25 g, 126 mmol) and platinum oxide (2.4 g) in acetic acid (250 ml) was hydrogenated for 2 hr. The catalyst was removed and the solution concentrated in vacuo. The residue was dissolved in water and the solution basified with sodium hydroxide. The basic mixture was extracted with ether. The extracts were dried and concentrated in vacuo. The residue was vacuum distilled to give 4-(3-methoxy-benzyl)piperidine as an oil (22.6 g, 88%). A sample of the hydrochloride was prepared in ether (mp: 146°–147° C.).

Calcd for $C_{13}H_{19}NO \cdot HCl$: C, 64.59%; H, 8.34%; N, 5.80%. Found: C, 64.38%; H, 8.34%; N, 5.66%.

EXAMPLE 2

3-[(3-Methoxyphenyl)methyl]piperidine hydrochloride

This compound was prepared according to the procedures described in Example 1 starting with 3-bromoanisole (18.7 g, 100 mmol), magnesium (2.4 g, 100 mmol) and 3-pyridinecarboxaldehyde (10.7 g, 100 mmol). The overall yield of product was 16.6 g (81%). A sample of the hydrochloride was prepared in ether (mp: 137°–140° C.).

Calcd for $C_{13}H_{19}NO \cdot HCl$: C, 64.59; H, 8.34; N, 5.79. Found: C, 64.36; H, 8.15; N, 5.74.

EXAMPLE 3

4-[(2-Fluoro-5-methoxyphenyl)methyl]piperidine
Step 1

Butyllithium (47.5 ml of 2.22M solution, 106 mmol) was added slowly to a solution of pentamethyldiethylenetriamine (15 ml) and 4-fluoroanisole (12.61 g, 0.1 mol) in THF (150 ml) at −70° C. The solution was stirred for 2 hr at −75° C. and a solution of pyridine-4-carboxaldehyde (9.55 ml, 0.1 mol) in THF was added at −75° C. The mixture was allowed to warm to 25° C. slowly and then quenched with ammonium chloride solution. The mixture was diluted with ethyl acetate and the organic layer was separated. The organic layer was washed with water and 3N hydrochloric acid. The acid washes were then basified with sodium hydroxide and extracted with ether and the ether solution concentrated in vacuo. The crude product was recrystallized from 80% ethanol to give (2-fluoro-5-methoxy-phenyl)-4-pyridylmethanol as a white powder (12.22 g+3.12 g second crop, 66% total yield).

Step 2

A mixture of (2-fluoro-5-methoxyphenyl)-4-pyridylmethanol and 10% palladium on charcoal in trifluoroacetic acid was hydrogenated using a process similar to step 2 of the previous example. The catalyst was removed and the solution concentrated in vacuo. The residue was dissolved in water and basified with sodium hydroxide. The basic mixture was extracted with ether and the ether extracts concentrated in vacuo. The crude 4-(2-fluoro-5-methoxybenzyl)pyridine was used without purification in the next step.

Step 3

A mixture of 4-(2-fluoro-5-methoxybenzyl)pyridine (7.7 g, 35.5 mmole) and platinum oxide (0.7 g) in acetic acid (75 ml) was hydrogenated for 3 hr. The catalyst was removed and the acetic acid removed in vacuo. The residue was dissolved in water and the solution basified with sodium hydroxide. The basic mixture was extracted with ether. The extracts were dried and concentrated in vacuo. The residue was vacuum distilled to give the product (6g, 76%).

B. PREPARATION OF PRODUCTS (I)

EXAMPLE 4

A general description of Process #1 is as follows:

A solution of the appropriate acid chloride (5.1 mmol) in dry acetonitrile (5 mL) was added dropwise to a stirred suspension of the benzylpiperidine (5.00 mmol) and micropulverized $K_2CO_3$ (15 mmol) in anhydrous acetonitrile (15 mL) at 5° C. The suspension was stirred 0.5 h at 5° C., and then 18 h at room temperature. The suspension was poured over ice (50 g) and partitioned between water (50 mL) and diethyl ether (100 mL). The organic layer was separated, and the aqueous layer was back-extracted with fresh diethyl ether (3×100 mL). The organic extracts were combined and washed with 5% HCl (200 mL), 5% NaOH (200 mL), water (200 mL), saturated brine (200 mL). The organic solution was dried over $K_2CO_3$, filtered, and then concentrated in vacuo to an oil. This crude product was purified by Kütigelrohr distillation (0.2 torr, 120°–200° C.) to give the product.

EXAMPLE 5

A specific example of Process #1 is as follows:

1-(Cyclopropylcarbonyl)-4-[(2-fluoro-5-methoxyphenyl)methyl]piperidine A magnetically stirred suspension of the amine (0.908 g, 4.07 mmol) and micropulverized anhydrous potassium carbonate (1.65 g, 11.9 mmol) in anhydrous acetonitrile (15 mL) at room temperature was treated dropwise with a solution of cyclopropane carboxylic acid (0.469 g, 4.40 mmol) in dry acetonitrile (5 mL). The suspension was stirred for 48 h. The suspension was poured over ice (50 g), treated with water (50 mL) and dichloromethane (50 mL). The layers were separated, the aqueous phase was back-extracted with fresh dichloromethane (3×50 mL), and the combined organic portions were washed with hydrochloric acid solution (1N, 200 mL), sodium hydroxide solution (1N, 200 mL), saturated brine (200 mL), dried ($K_2CO_3$), filtered, and concentrated in vacuo to an oil. Kütigelrohr distillation (0.2 torr, 120°–200° C. ) gave the product as a clear oil in 91% yield: IR (film) 3006, 2932, 1636, 1270, 1210, 1034 cm$^{-1}$; $^1$H NMR (CDCl$_3$) δ6.86 (t, J=9.0 Hz, 1H), 6.65–6.57 (m, 2H), 4.51 (bd, J=12.6 Hz, 1H), 4.12 (bd, J=13.0 Hz, 1H), 3.70 (s, 3H), 2.95 (t, J=12.6 Hz, 1H), 2.49 (dd, J=7.2, 1.0 Hz, 2H), 2.47 (t, J=13 Hz, 1H), 1.82–1.59 (m, 4H), 1.19–1.10 (m, 2H), 0.91–0.86 (m, 2H), 0.69–0.62 (m, 2H); $^{13}$C NMR (CDCl$_3$) δ171.6, 155.6 (d, J=237.0 Hz), 155.4, 116.5 (d, J=4.6 Hz), 115.5 (d, J=24.1 Hz), 112.1 (d, J=8.2 Hz), 55.6, 45.7, 42.4, 37.3, 36.1, 32.6, 31.7, 11.0, 7.2; MS m/z 292 (M$^+$+1, free base).

Calcd for C$_{17}$H$_{22}$FNO$_2$. 0.13H$_2$O: C, 69.52; H, 7.64; N, 4.77. Found: C, 69.54; H, 7.64; N, 4.68.

EXAMPLE 6

A specific example of Process #2 is as follows:

4-[(2-Fluoro-5-methoxyphenyl)methyl]-1-(2-methyl-1-oxobutyl)piperidine N,N'-carbonyldiimidazole (0.681 g, 4.20 mmol) was slowly added to a stirred solution of 2-methylbutyric acid (0.409 g, 3.92 mmol) in 15 mL anhydrous CH$_2$Cl$_2$ at room temperature. The solution was heated to reflux for 2 h and then cooled to room temperature. A solution of 4-(2-fluoro-5-methoxybenzyl)piperidine (4 mmol) in dry CH$_2$Cl$_2$ (5 mL) was added to the reaction mixture. After stirring for 72 h, the solution was partitioned between CH$_2$Cl$_2$ (250 mL) and water (250 mL). The organic layer was separated, and the aqueous layer was back-extracted with fresh CH$_2$Cl$_2$ (3×100 mL). The organic extracts were combined and washed with 5% hydrochloric acid solution (200 mL), 5% sodium hydroxide solution (200 ml), water (200 mL), and saturated brine (200 mL). The organic solution was dried over K$_2$CO$_3$, filtered, and then concentrated in vacuo to an oil. This crude product was purified by Kütigelrohr distillation (0.2 torr, 120°–200° C.). Clear oil, yield: 79%. IR (film) 2934, 1638, 1272 1228, 1210, 1036, 814 cm$^{-1}$; $^1$H NMR (CDCl$_3$) δ6.81 (t, J=9.0 Hz, 1H), 6.60–6.53 (m, 2H), 4.54 (bd, J=12.7 Hz, 1H), 3.82 (bd, J=13.2 Hz, 1H), 3.65 (s, 3H), 2.84 (bt, J=12.8 Hz, 1H), 2.52 (sextet, J=6.8 Hz, 1H)), 2.43 (d, J=6.8 Hz, 1H), 2.38 (bt, J=13.0 Hz, 1H), 1.73–1.57 (m, 4H), 1.34–1.23 (m, 1H), 1.06 (qd, J=12.1, 4.0 Hz, 2H). 0.98 (t, J=8.1 Hz, 3H), 0.77 (q, J=8.0 Hz, 3H); $^{13}$C NMR (CDCl$_3$) δ174.6, 155.5 (d, J=237.1 Hz), 155.4 (d, J=1.6 Hz), 127.5 (d, J=18.0 Hz), 116.4 (d, J=4.6 Hz), 115.5 (d, J=24.7 Hz), 112.1 (d, J=8.0 Hz), 55.5, 45.6, 41.9 (d, J=7.2 Hz), 37.2, 36.8, 36.0, 32.8 (d, J=2.7 Hz), 31.9 (d, J=17.5 Hz), 27.0, 17.2 (d, J=16.6 Hz), 11.9 (d, J=5.3 Hz); MS m/z 308 (M$^+$+1, free base).

Calcd for C$_{18}$H$_{26}$FNO$_2$. 0.11 H$_2$O: C, 69.88; H, 8.54; N, 4.53. Found: C, 69.88; H, 8.56; N, 4.56.

EXAMPLE 7

A general description of Process #3 is as follows:

A solution of the appropriate isocyanate or isothiocyanate in dry CH$_2$Cl$_2$ (5 mL) was added to a stirred solution of the benzylpiperidine (4 mmol) in anhydrous CH$_2$Cl$_{12}$ (15 mL) at 5 ° C. The suspension was stirred 0.5 h at 5 ° C., and then for 48 h at room temperature. The suspension was poured over ice (50 g), and partitioned between water (200 mL) and CH$_2$Cl$_2$ (250 mL). The organic layer was separated, and the aqueous layer was back-extracted with fresh CH$_2$Cl$_{12}$ (3×100 mL). The organic extracts were combined and washed with 5% HCl (200 mL), 5% NaOH (200 mL), water (200 mL), and saturated brine (200 mL). The organic solution was dried over K$_2$CO$_3$, filtered, and concentrated in vacuo to an oil. Drying in vacuo at 60°–80° C. gave the desired product.

A specific example of Process #3 is as follows:

EXAMPLE 8

N-Ethyl-4-[(2-fluoro-5-methoxyphenyl)methyl]-1-piperidinecarboxamide

A magnetically stirred solution of 4-[(2-fluoro-5-methoxyphenyl)methyl]piperidine (0.895 g, 4.01 mmol) in anhydrous dichloromethane (15 mL) at 5° C. was treated dropwise with a solution of ethyl isocyanate (0.320 g, 4.41 mmol) in dry dichloromethane (5 mL). The solution was stirred 0.5 h at 5° C., allowed to warm to room temperature and stirred for 48 h. The solution was poured over ice (50g), and treated with water (200 mL) and dichloromethane (250 mL). The layers were separated, the aqueous phase was back-extracted with fresh dichloromethane (3×200 mL), and the combined organic portions were washed with 1N hydrochloric acid solution (350 mL), 5% sodium hydroxide solution (400 mL), water (400 mL), saturated brine (400 mL), dried is (K$_2$CO$_3$), filtered, and concentrated in vacuo. Drying (85° C.) in vacuo gave 1.08 g (92%) of the desired product as a clear oil: IR (film) 3346, 2930, 1622, 1592, 1538, 1498, 1274, 1252; 1214, 1036 cm$^{-1}$; $^1$H NMR (CDCl$_3$) δ6.90 (t, J=9.0 Hz, 1H), 6.69–6.60 (m, 2H), 4.50 (bt, J=4.7 Hz, 1H), 3.89 (bd, J=13.2 Hz, 2H), 3.74 (s, 3H), 3.27–3.17 (m, 2H), 2.67 (td, J=12.8, 2.4 Hz, 2H), 2.52 (dd, J=7.1, 1.1 Hz, 2H), 1.74–1.61 (m, 1H), 1.62 (bd, J=13.5 Hz, 2H), 1.18 (qd, J=12.0, 4.0 Hz, 2H), 1.10 (t, J=7.2 Hz, 3H); $^{13}$C NMR (CDCl$_3$)δ57.7, 155.7 (d, J=237.1 Hz), 155.4 (d, J=1.7 Hz), 127.8 (d, J=18.0 Hz), 116.6 (d, J=5.1 Hz), 115.5 (d, J=24.7 Hz), 112.1 (d, J=8.0 Hz), 55.7, 44.1, 37.0, 36.2, 35.7, 31.7, 15.6; MS m/z 295 (M$^+$+1, free base).

Calcd for C$_{16}$H$_{23}$FN$_2$O$_2$: C, 65.28; H, 7.88; N, 9.52. Found: C, 64.96; H, 7.94; N, 9.52.

Physical/chemical data pertaining to additional examples of Formula I compounds that were prepared by Processes 1–3 are listed in Table 1.

TABLE 1

Structure: R-N-piperidine with CH2 at position 4 connected to phenyl ring having (F)n and OCH3 substituents.

| Ex. No. | R | Substit. at ring pos.: | n | Prep. Process | Compound Formula (% yield) | Elemental analysis Calcd | Elemental analysis Found |
|---|---|---|---|---|---|---|---|
| 5 | cyclopropyl-C(O)— | 4 | 1 | 1 | $C_{17}H_{22}FNO_2 \cdot 0.13H_2O$ (91) | C, 69.52<br>H, 7.64<br>N, 4.77 | C, 69.54<br>H, 7.64<br>N, 4.68 |
| 6 | (CH3)(C2H5)CH—C(O)— | 4 | 1 | 2 | $C_{18}H_{26}FNO_2 \cdot 0.11H_2O$ (79) | C, 69.88<br>H, 8.54<br>N, 4.53 | C, 69.88<br>H, 8.56<br>N, 4.56 |
| 8 | C2H5HN—C(O)— | 4 | 1 | 3 | $C_{16}H_{23}FN_2O_2$ (92) | C, 65.28<br>H, 7.88<br>N, 9.52 | C, 64.96<br>H, 7.94<br>N, 9.52 |
| 10 | cyclopropyl-C(O)— | 4 | 0 | 1 | $C_{17}H_{23}NO_2 \cdot 0.2H_2O$ (74) | C, 73.72<br>H, 8.52<br>N, 5.06 | C, 73.92<br>H, 8.45<br>N, 5.01 |
| 11 | (CH3)2CH—C(O)— | 4 | 1 | 1 | $C_{17}H_{24}FNO_2$ (94) | C, 69.60<br>H, 8.25<br>N, 4.78 | C, 69.24<br>H, 8.47<br>N, 4.78 |
| 12 | H2C=HC—C(O)— | 4 | 1 | 1 | $C_{16}H_{20}FNO_2 \cdot 0.28H_2O$ (48) | C, 68.05<br>H, 7.34<br>N, 4.96 | C, 68.04<br>H, 7.30<br>N, 5.21 |
| 13 | C2H5—C(O)— | 4 | 1 | 1 | $C_{16}H_{22}FNO_2 \cdot 0.17H_2O$ (94) | C, 68.04<br>H, 7.97<br>N, 4.96 | C, 68.02<br>H, 7.76<br>N, 5.19 |
| 14 | CH3(CH2)2—C(O)— | 4 | 1 | 1 | $C_{17}H_{24}FNO_2 \cdot 0.17H_2O$ (91) | C, 68.88<br>H, 8.28<br>N, 4.73 | C, 68.99<br>H, 8.13<br>N, 4.89 |
| 15 | cyclobutyl-C(O)— | 4 | 1 | 1 | $C_{18}H_{24}FNO_2 \cdot 0.16H_2O$ (91) | C, 70.13<br>H, 7.95<br>N, 4.54 | C, 70.13<br>H, 7.98<br>N, 4.57 |
| 16 | CH3(CH2)2—C(O)— | 4 | 0 | 1 | $C_{17}H_{25}NO_2 \cdot 0.5H_2O$ (35) | C, 71.80<br>H, 9.22<br>N, 4.93 | C, 71.90<br>H, 9.20<br>N, 4.87 |
| 17 | CH3—C(O)— | 4 | 1 | 1 | $C_{15}H_{20}FNO_2$ (95) | C, 67.90<br>H, 7.60<br>N, 5.28 | C, 67.87<br>H, 7.64<br>N, 5.18 |
| 18 | CH3CH=CH—C(O)— | 4 | 1 | 1 | $C_{17}H_{22}FNO_2 \cdot 0.25H_2O$ (91) | C, 69.01<br>H, 7.67<br>N, 4.73 | C, 69.00<br>H, 7.66<br>N, 4.61 |
| 19 | cyclopentyl-C(O)— | 4 | 1 | 1 | $C_{19}H_{26}FNO_2$ (89) | C, 71.44<br>H, 8.21<br>N, 4.39 | C, 71.62<br>H, 8.24<br>N, 4.41 |
| 20 | CH3HN—C(O)— | 4 | 1 | 3 | $C_{15}H_{21}FN_2O_2$ (53) | C, 64.26<br>H, 7.55<br>N, 9.99 | C, 64.01<br>H, 7.58<br>N, 9.86 |
| 21 | CH3HN—C(O)— | 4 | 0 | 3 | $C_{15}H_{22}N_2O_2 \cdot 0.15 H_2O \cdot 0.15CH_2CL_2$ (87) | C, 65.51<br>H, 8.21<br>N, 10.09 | C, 65.26<br>H, 8.24<br>N, 10.52 |

TABLE 1-continued

[Structure: R-N-(piperidine ring with positions 3,4)-CH$_2$-phenyl(F)$_n$-OCH$_3$]

| Ex. No. | R | Substit. at ring pos.: | n | Prep. Process | Compound Formula (% yield) | Elemental analysis Calcd | Found |
|---|---|---|---|---|---|---|---|
| 22 | C$_2$H$_5$HN—C(=O)— | 4 | 0 | 3 | C$_{16}$H$_{24}$N$_2$O$_2$·0.3H$_2$O (91) | C, 68.21 H, 8.80 N, 9.95 | C, 67.85 H, 8.49 N, 9.77 |
| 23 | CH$_3$(CH$_2$)$_2$HN—C(=O)— | 4 | 1 | 3 | C$_{17}$H$_{25}$FN$_2$O$_2$ (48) | C, 66.21 H, 8.17 N, 9.08 | C, 66.27 H, 8.09 N, 9.08 |
| 24 | (CH$_3$)$_2$N—C(=O)— | 4 | 1 | 1 | C$_{16}$H$_{23}$FN$_2$O$_2$· 0.17H$_2$O (85) | C, 64.61 H, 7.91 N, 9.42 | C, 64.61 H, 7.87 N, 9.56 |
| 25 | CH$_3$(CH$_2$)$_2$HN—C(=S)— | 4 | 1 | 3 | C$_{17}$H$_{25}$FN$_2$O$_1$S (87) | C, 62.93 H, 7.77 N, 8.63 | C, 62.54 H, 7.65 N, 8.73 |
| 26 | CH$_3$(CH$_2$)$_2$—C(=O)— | 3 | 0 | 1 | C$_{17}$H$_{25}$NO$_2$ (86) | C, 74.14 H, 9.15 N, 5.09 | C, 73.81 H, 8.85 N, 5.24 |
| 27 | C$_2$H$_5$HN—C(=O)— | 3 | 0 | 3 | C$_{16}$H$_{24}$N$_2$O$_2$·0.1H$_2$O (68) | C, 69.08 H, 8.77 N, 10.07 | C, 68.84 H, 8.39 N, 10.14 |

EXAMPLE 9

Measurement of Melatonergic Binding

1. Reagents
   (a) 50 mM Tris buffer containing 12.5 mM MgCl$_2$, and 2 mM EDTA, pH 7.4 at 37° C. with concentrated HCl.
   (b) Wash buffer: 20 mM Tris base containing 2 mM MgCl$_2$.pH 7.4 at room temperature.
   (c) 10$^{-4}$ M 6-Chloromelatonin (10$^{-5}$ M final concentration).
   (d) 2-[$^{125}$I]-iodomelatoin, 44 pM final concentration
   Source: NEN
   Calculations: Concentration of stock:
       Specific Activity = 2200 Ci/mMol
       Concentration = 236 mCi/ml
       Concentration of stock = (236 × 10$^{-6}$ Ci/ml)/(2200 Ci/mMol) = 107.3 nM
   cmp/20 ml
   (conc.) (liters/tube) = (0.44 × 10$^{-9}$ m/L) (20 × 10$^{-6}$ L) = 8.8 × 10$^{-15}$ m × 1000 ×
   by specific activity (8.8 × 10$^{-12}$ mM) (2200 Ci/mMol) = 1.93 × 10$^{-8}$ Ci ×
   by decay factor (1.93 × 10$^{-8}$ Ci) (1 on day made) = 1.93 × 10$^{-8}$ Ci ×
   by dpm/Ci constant (1.93 × 10$^{-8}$) (2.22 × 10$^{12}$ dpm/Ci) = 42979 dpm × 0.75 (machine efficiency) = 32234 cpm 2. Tissue preparation. Male New Zealand white rabbits (Hazelton Research) are decapitated, the brains are rapidly removed and chilled. The parietal cortex is crudely dissected and frozen on dry ice with tissue stored at −80° C. until assayed. Tissue is weighed and thawed in 20 mls ice cold Tris buffer (a) and homogenized by treatment with a polytron for 10 seconds at setting 17. Ice cold Tris (a) is added to a volume of 40 mls. The homogenate is centrifuged in a Sorvall-SS-34 head at 19,000 rpm (44,000×g) for 20 min at 4° C. The resulting supernatant is decanted and discarded. The pellet is rehomogenized in an additional 20 mls of Tris, diluted and centrifuged as before. The supernatant is decanted and discarded. The resulting pellet is homogenized in 20 volumes of Tris per gram of original tissue (a 1:20 homogenate), chilled, and held on ice until assayed.

| | Tube # | Buffer (a) | 10$^{-4}$ M 6-Chloro-melatonin | Experimental Compound | 2-[125I]-iodo-melatonin | Tissue Homogenate (1:20) |
|---|---|---|---|---|---|---|
| Total | 1, 2 | 20 ml | — | — | 20 ml | 160 ml |
| Blank | 3, 4 | — | 20 ml | — | 20 ml | 160 ml |

| Tube # | Buffer (a) | $10^{-4}$ M 6-Chloro-melatonin | Experimental Compound | 2-[125I]-iodo-melatonin | Tissue Homogenate (1:20) |
|---|---|---|---|---|---|
| Unknowns 5, 6 | — | — | 20 ml conc. 1 | 20 ml | 160 ml |
| 7, 8 | — | — | 20 ml conc. 2 | 20 ml | 160 ml |

4. Incubation: 37° C. for 1 hour. Reaction is terminated by filtration through a Brandel cell harvester. Filters are washed 3 times.

5. Activity: Compounds with an $IC_{50}$ value less than 250 nM are termed active within the context of the present invention.

6. References: Stankov, B., Cozzi, B., Lucini, V., Fumagalli, P., Scaglione, F. and F. Fraschini. Characterization and mapping of melatonin receptors in the brain of three mammalian species: Rabbit, horse, and sheep. Neuroendocrinology 53: 214–221, 1991.

Reasonable variations, such as those which would occur to a skilled artisan, can be made herein without departing from the scope of the invention.

We claim:

1. A compound of Formula I

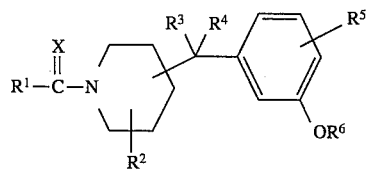

wherein $R^1$ is selected from lower $C_{1-4}$ alkyl, $C_{2-4}$ alkenyl, $C_{3-6}$ cycloalkyl, and $NR^7R^8$ where $R^7$ and $R^8$ are independently selected from hydrogen and $C_{1-4}$ alkyl with the proviso that $R^7$ and $R^8$ are not both hydrogen;

$R^2$, $R^3$ and $R^4$ are independently selected from hydrogen and $C_{1-4}$ alkyl;

$R^5$ is hydrogen, $C_{1-4}$ alkyl, halogen, or trifluoromethyl;

$R^6$ is $C_{1-4}$ alkyl;

X is either oxygen or sulfur; and and the substituted phenyl alkyl moiety of formula 1 and appended to either the 3- or 4-position of the piperidinyl ring with the proviso that when $R^5$ is H, $R^1$ can not be $C_{1-2}$ alkyl.

2. The compound of claim 1 wherein $R^2$, $R^3$ and $R^4$ are hydrogen.

3. The compound of claim 2 in which $R^5$ is hydrogen or fluoro; with the proviso that, when F is in the 2-position, $OR^6$ is para to F.

4. The compound of claim 3 wherein $R^6$ is methyl.

5. The compound of claim 4 selected from the group consisting of:

1-Acetyl-4-[(2-fluoro-5-methoxyphenyl)methyl]piperidine;

4-[(2-Fluoro-5-methoxyphenyl)methyl]-1-(2-methyl-1-oxopropyl)piperidine;

4-[(2-Fluoro-5-methoxyphenyl)methyl]-1-(1-oxobutyl)piperidine;

4-[(2-Fluoro-5-methoxyphenyl)methyl]-1-(1-oxopropyl)piperidine;

4-[(2-Fluoro-5-methoxyphenyl)methyl]-1-(1-oxo-2-propenyl)piperidine;

(E)-4-[(2-Fluoro-5-methoxyphenyl)methyl]-1-(1-oxo-2-butenyl)piperidine; and

4-[(2-Fluoro-5-methoxyphenyl)methyl]-1-(2-methyl-1-oxobutyl)piperidine.

6. The compound of claim 4 wherein $R^1$ is $C_{3-6}$ cycloalkyl.

7. The compound of claim 6 selected from the group consisting of:

1-(Cyclopropylcarbonyl)-4-[(2-fluoro-5-methoxyphenyl)methyl]piperidine;

1-(Cyclobutylcarbonyl)-4-[(2-fluoro-5-methoxyphenyl)methyl]piperidine; and 1-(Cyclopentylcarbonyl)-4-[(2-fluoro-5-methoxyphenyl)methyl]piperidine.

8. The compound of claim 4 wherein R is $NR^7R^8$.

9. The compound of claim 8 selected from the group consisting of:

4-[(2-Fluoro-5-methoxyphenyl)methyl]-N,N-dimethyl-1-peridinecarboxamide;

4-[(2-Fluoro-5-methoxyphenyl)methyl]-N-methyl-1-piperidinecarboxamide;

4-[(2-Fluoro-5-methoxyphenyl)methyl]-N-propyl-1-piperidinecarboxamide;

N-Ethyl-4-[(2-fluoro-5-methoxyphenyl)methyl]-1-piperidinecarboxamide; and

4-[(2-Fluoro-5-methoxyphenyl)methyl]-N-propyl-1-piperidinecarbothioic acid amide.

10. The compound of claim 4 wherein $R^5$ is H and $R^1$ can not be $C_{1-2}$ alkyl.

11. The compound of claim 10 selected from the group consisting of:

1-(Cyclopropylcarbonyl)-4-[(3-methoxyphenyl)methyl]piperidine;

4-[(3-Methoxyphenyl)methyl]-1-(1-oxobutyl)piperidine;

N-Ethyl-4-[(3-methoxyphenyl)methyl]-1-piperidinecarboxamide;

4-[(3-Methoxyphenyl)methyl]-N-methyl-1-piperidinecarboxamide;

3-[(3-Methoxyphenyl)methyl]-1-(1-oxobutyl)piperidine; and

N-Ethyl-3-[(3-methoxyphenyl)methyl]-1-piperidinecarboxamide.

12. The compound of claim 1, 4-[(2-Fluoro-5-methoxyphenyl)methyl]-1-(2-methyl-1 -oxopropyl)piperidin.

13. The compound of claim 1, 1-(Cyclopropylcarbonyl)-4-[(2-fluoro-5-methoxyphenyl)methyl]piperidine.

14. The compound of claim 1, 1-(Cyclopropylcarbonyl)-4-[(3-methoxyphenyl)methyl]piperidine.

15. The compound of claim 1, N-Ethyl-4-[(3-methoxyphenyl)methyl]-1-piperidinecarboxamide.

16. The compound of claim 1, 4-[(3-Methoxyphenyl)methyl]-N-methyl-1-piperidinecarboxamide.

17. The compound of claim 1, 4-[(2-Fluoro-5-methoxyphenyl)methyl]-N-methyl- 1-piperidinecarboxamide.

18. The compound of claim 1, N-Ethyl-[(2-fluoro-5-methoxyphenyl)methyl]-1-piperidinecarboxamide.

19. A pharmaceutical composition for treating a sleep or circadian rhythm disorder in a patient in need thereof comprising an effective amount of a compound of claim 1 and a suitable amount of a pharmaceutically acceptable carrier.

20. A method of treating a sleep or circadian rhythm disorder in a patient in need of such treatment comprising the administration of an effective amount of a compound of claim 1.

* * * * *

UNITED STATES PATENT AND TRADEMARK OFFICE
CERTIFICATE OF CORRECTION

PATENT NO: 5,530,012
DATED    : June 25, 1996
INVENTOR(S): Mattson, et al.

It is certified that error appears in the above-identified patent and that said Letters Patent is hereby corrected as shown below:

In claim 1, column 17, line 44, after "sulfur;" delete "and".

In claim 1, column 17, line 45, after "formula 1" delete "and" and replace it with --is--.

In claim 9, column 18, line 28, delete "peridinecarboxamide" and replace it with --piperidinecarboxamide--.

In claim 12, column 18, line 55, after "-oxopropyl)" delete "piperidin" and replace it with --piperidine--.

Signed and Sealed this

First Day of October, 1996

BRUCE LEHMAN

*Attest:*

*Attesting Officer*    Commissioner of Patents and Trademarks